(12) United States Patent
Wittmer

(10) Patent No.: US 7,587,953 B2
(45) Date of Patent: Sep. 15, 2009

(54) PLUGGABLE MODULE FOR A LIQUID OR GAS SENSOR

(75) Inventor: Detlev Wittmer, Maulbronn (DE)

(73) Assignee: Endress + Hauser Conducta Gesellschaft fur Mess- und Regeltechnik mbH + Co. KG, Gerlingen (DE)

( * ) Notice: Subject to any disclaimer, the term of this patent is extended or adjusted under 35 U.S.C. 154(b) by 15 days.

(21) Appl. No.: 10/572,797

(22) PCT Filed: Sep. 20, 2004

(86) PCT No.: PCT/EP2004/010523

§ 371 (c)(1),
(2), (4) Date: Apr. 23, 2007

(87) PCT Pub. No.: WO2005/031339

PCT Pub. Date: Apr. 7, 2005

(65) Prior Publication Data

US 2008/0034864 A1 Feb. 14, 2008

(30) Foreign Application Priority Data

Sep. 23, 2003 (DE) ................. 103 44 262

(51) Int. Cl.
*G01D 5/12* (2006.01)
*G01D 5/48* (2006.01)
(52) U.S. Cl. ............ 73/866.1; 73/31.05; 73/53.01
(58) Field of Classification Search ............ 73/37, 73/866.1, 23.2, 31.05, 53.01; 436/43
See application file for complete search history.

(56) References Cited

U.S. PATENT DOCUMENTS

| 5,844,472 | A | * | 12/1998 | Lee | 340/438 |
| 6,053,031 | A | * | 4/2000 | Kullik et al. | 73/31.05 |
| 6,850,788 | B2 | * | 2/2005 | Al-Ali | 600/323 |
| 6,893,396 | B2 | * | 5/2005 | Schulze et al. | 600/300 |
| 6,966,880 | B2 | * | 11/2005 | Boecker et al. | 600/583 |
| 7,088,235 | B1 | * | 8/2006 | Carricut | 340/539.12 |
| 7,142,107 | B2 | * | 11/2006 | Kates | 340/539.1 |
| 2002/0027085 | A1 | * | 3/2002 | Stori et al. | 205/775 |
| 2003/0102872 | A1 | | 6/2003 | Honda | |
| 2003/0224523 | A1 | * | 12/2003 | Thornberg et al. | 436/43 |
| 2004/0119591 | A1 | * | 6/2004 | Peeters | 340/539.26 |
| 2005/0185438 | A1 | * | 8/2005 | Ching | 365/52 |
| 2006/0219776 | A1 | * | 10/2006 | Finn | 235/380 |
| 2006/0254911 | A1 | * | 11/2006 | Lindmueller et al. | 204/424 |
| 2009/0013107 | A1 | * | 1/2009 | Wittmer | 710/69 |

FOREIGN PATENT DOCUMENTS

| CA | 2086288 A1 * | 6/1993 |
| CA | 2360902 A1 * | 5/2002 |
| DE | 41 43 092 A1 | 7/1993 |
| DE | 690 31 456 T2 | 2/1998 |

(Continued)

*Primary Examiner*—Thomas P Noland
(74) *Attorney, Agent, or Firm*—Bacon & Thomas, PLLC

(57) ABSTRACT

For a liquid-, or gas-, sensor composed of a sensor module SM and a sensor module head SMK, which are pluggably connectable together and which enable when plugged together an exchange of data and energy via a galvanically decoupled, transfer zone, a pluggable module ST1, or ST2, as the case may be, is provided, which is connectable with the sensor module SM, or with the sensor module head SMK, and which serves for display of sensor data stored in the sensor module SM, or for simulation of a measured value.

5 Claims, 3 Drawing Sheets

FOREIGN PATENT DOCUMENTS

| | | |
|---|---|---|
| DE | 197 22 744 A1 | 12/1998 |
| DE | 102 18 606 A1 | 11/2003 |
| EP | 433995 A2 * | 6/1991 |
| EP | 1 143 239 A | 10/2001 |
| EP | 1 206 012 A | 5/2002 |
| GB | 2361947 A * | 11/2001 |
| WO | WO 96/12946 A | 5/1996 |
| WO | WO 01/14873 A1 | 3/2001 |
| WO | WO 0143098 A2 * | 6/2001 |
| WO | WO 2004/086030 A1 | 10/2004 |

\* cited by examiner

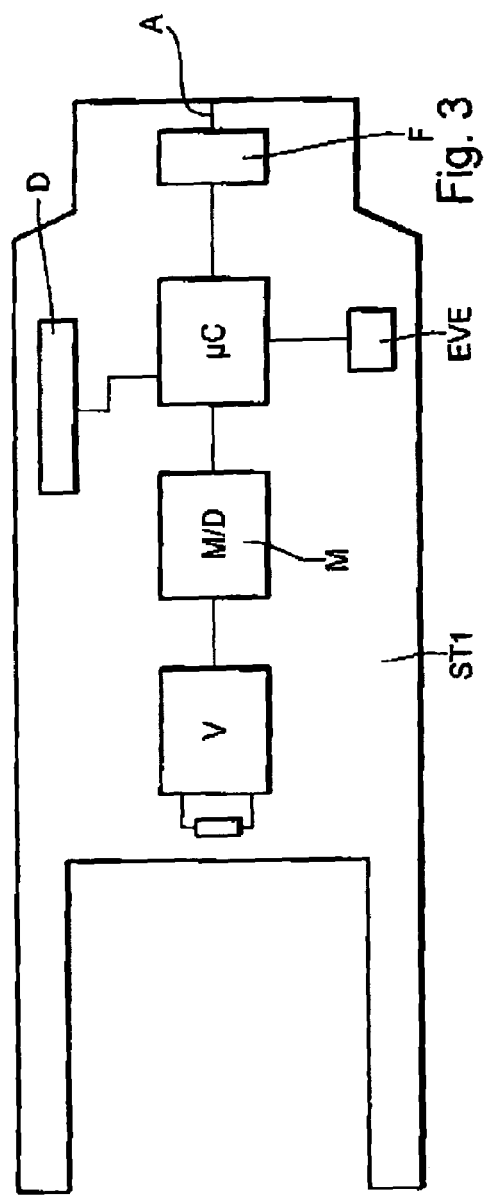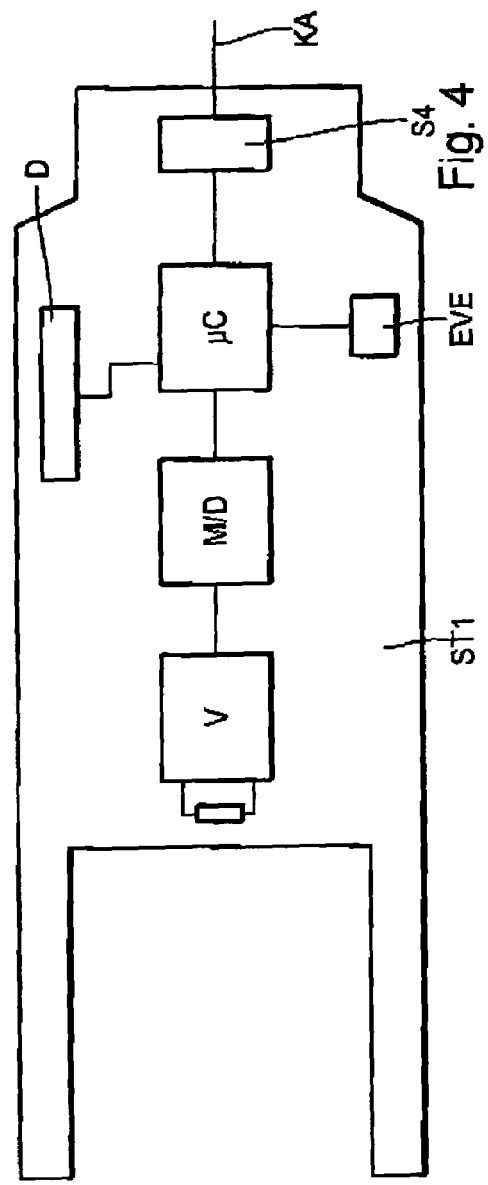

PLUGGABLE MODULE FOR A LIQUID OR GAS SENSOR

FIELD OF THE INVENTION

The present invention relates to a pluggable module for a liquid or gas sensor. Liquid or gas sensors are used for measuring pH-values or redox potentials, temperatures, conductivities or turbidities of liquids.

BACKGROUND OF THE INVENTION

In the following, reference will be essentially to potentiometric sensors, as an example of a liquid, or gas, sensor. Potentiometric sensors are used above all for determining potentials at large resistances, such as is the case for pH-measurements and redox-measurements. With the help of pH-electrodes, or redox-electrodes, as the case may be, the potentials of solutions are sensed.

These electrodes are exposed to strong wear in many cases of application, so that they must frequently be replaced after a short time of operation.

There exist very simply constructed pH-sensors, which consist only of a pH-electrode, without any electronic components. These pH-electrodes deliver a pH-dependent potential, which can be accessed on suitable, electrical connections. Optionally, these pH-electrodes have an integrated temperature sensor, e.g. PT100, for temperature compensation. The potential of the temperature sensor can be accessed at suitable temperature outputs. For measuring, these pH-sensors are usually connected via a cable to a transmitter, which generates a measurement signal from the pH-dependent potential and, as required, from the temperature signal of the temperature sensor.

Besides the described, simple pH-electrodes, or sensors, there are also those with integrated preamplifier for impedance conversion. The output signal of the preamplifier is that potential of the pH-sensor, with, however, instead of the internal resistance of the pH-sensor, which lies in the order of magnitude of 100 M, now the internal resistance of the preamplifier of some few ohms being the determining factor. Consequently, the further transmission and processing of the output potential is considerably simplified for a transmitter. The preamplifier is either fed via a battery or supplied with voltage via a cable.

Furthermore, under the name Direct Line of the Honeywell company, simple transmitters are obtainable, which are mounted directly on the pH-sensors. In this way, it is possible to generate, in the immediate vicinity of the sensor, e.g. a 4-20 mA measurement signal, which can then be transmitted, without more, to the control room.

In the case of all known pH-electrodes, or pH-sensors, it is necessary to calibrate the electrodes after connection to the transmitter, in order to be able to store the determined calibration parameters in the transmitter. Sensor specific information, such as measuring point name, etc., are, as a rule, not obtainable on-site, thus in the immediate vicinity of the sensor.

Recently, a pH-sensor has become known (available from the firm of Endress+Hauser under the mark MemoSens), which is composed of a sensor module and a sensor module head, which can be plugged together. The data and energy transfer between sensor module and sensor module head occurs contactlessly via a connection zone, which serves for galvanic decoupling. Additionally, a digital memory is provided in the sensor module, for storing, among other things, calibration parameters.

Likewise, it is not possible to check, in simple manner, whether a pH-sensor is capable of functioning. In the control room, one must rely on a secure data transfer on the path from sensor to control room.

SUMMARY OF THE INVENTION

An object of the invention is, therefore, to provide, for a potentiometric sensor, a pluggable module, which does not exhibit the above-named disadvantages, which, especially, enables the presentation of sensor-specific information directly on-site, and which, additionally, enables a checking of the measured value sent to the control room and which is simply and cost-favorably manufacturable.

This object is achieved by the pluggable modules for potentiometric sensors as such modules; wherein the pluggable modules are connectable with the sensor modules and have a display unit which serves for display of sensor data stored in the sensor modules.

BRIEF DESCRIPTION OF THE DRAWINGS

The invention will now be explained in further detail on the basis of examples of embodiments presented in the drawing, the figures of which show as follows:

FIG. 3 schematic drawing of a pluggable module of the invention, in the form of a transmitter with display;

FIG. 4 pluggable module of the invention, with fieldbus connection;

DESCRIPTION OF THE PREFERRED EMBODIMENTS

Figure 1:
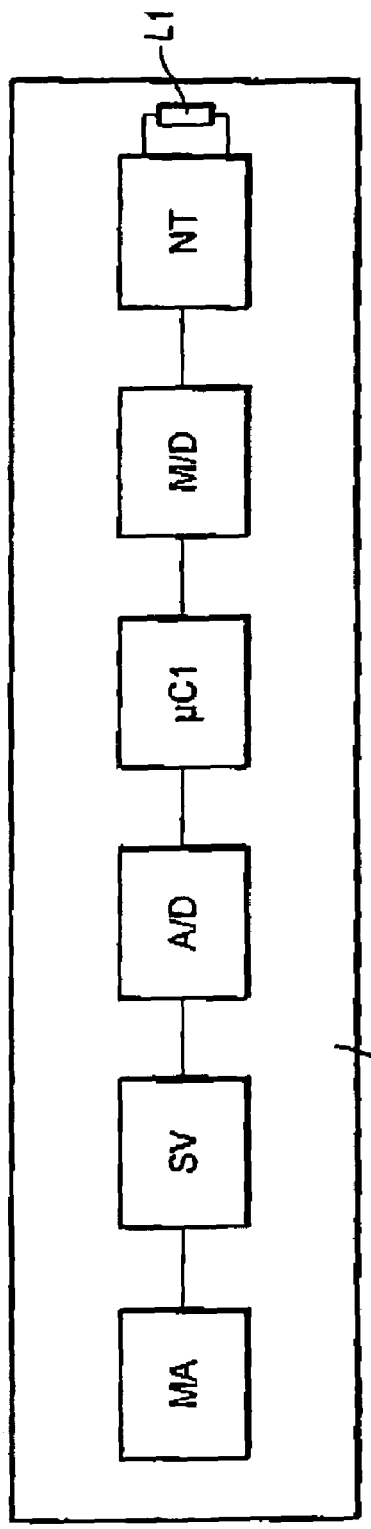
FIG. 1 schematic drawing of a sensor module.
Figure 2:
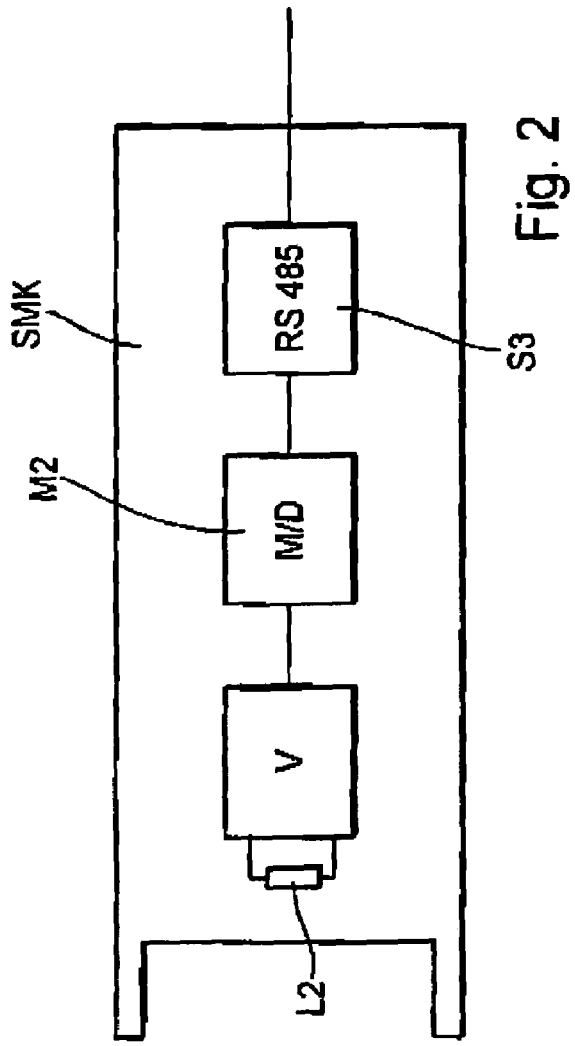
FIG. 2 schematic drawing of a sensor module head.

FIG. 1 shows a sensor module SM in greater detail. The sensor module SM is composed of a measured value pickup MA (e.g. a glass electrode), which is submerged into the liquid to be measured. The measured value pickup delivers an analog measurement signal, which is preprocessed in an analog signal processing unit SV. Then, the conditioned, analog measurement signal is converted in an analog/digital converter A/D to a digital value, which is processed further in a microcontroller μC1. The microcontroller μC1 is connected with a coil L1 via a modem M/D and a power supply NT. Via the power supply, the entire sensor module SM is provided with voltage. Embodied to fit the sensor module SM is a sensor module head SMK, which is shown in greater detail in FIG. 2. In the sensor module head SMK, a coil L2 is connected via an amplifier V with a modem M2, which, in turn, is connected with an interface S3. Interface S3 is a usual RS485 interface, which serves for data communication with a measurement converter/transmitter (not shown). Sensor module SM and sensor module head SMK are pluggably connectable together. Via the coils L1 and L2, both data and energy exchange can be effected. The two modules are, in this way, galvanically decoupled.

FIG. 3 shows a pluggable module ST1 of the invention, serving as a transmitter with display. Pluggable module ST1 has, like the sensor module head SMK, a coil L2, an amplifier V and a modem M2. In the case of pluggable module ST1, however, in contrast to the sensor model head SMK, no interface S3 is provided, but, instead, a microcontroller μC, which is connected with a display D and an energy, or power, supply unit EVE. Serving for the data transmission is a radio module F with antenna A. Radio module F is likewise connected to the microcontroller μC. The energy supply unit EVE can be a battery, or solar cells. The energy supply unit EVE also supplies the sensor module SM with voltage. On the display D, sensor-specific information, such as e.g. measuring point designation, can be displayed. To this end, the corresponding data are read out of the sensor module SM. If the pluggable module ST1 serves only for displaying sensor-specific information, then the radio unit F can be omitted. Alternatively, the display D can be omitted, when only a wireless data transfer to a superordinated unit is desired.

FIG. 4 presents an alternative embodiment of the pluggable module ST1, which is connectable with a fieldbus. Here, the microcontroller μC is not connected with a radio unit F, but, instead, with a fieldbus interface S4, which has a cable connection KA for a fieldbus. Interface S4 can be a Profibus-, Foundation Fieldbus-, or HART-interface.

Figure 5:
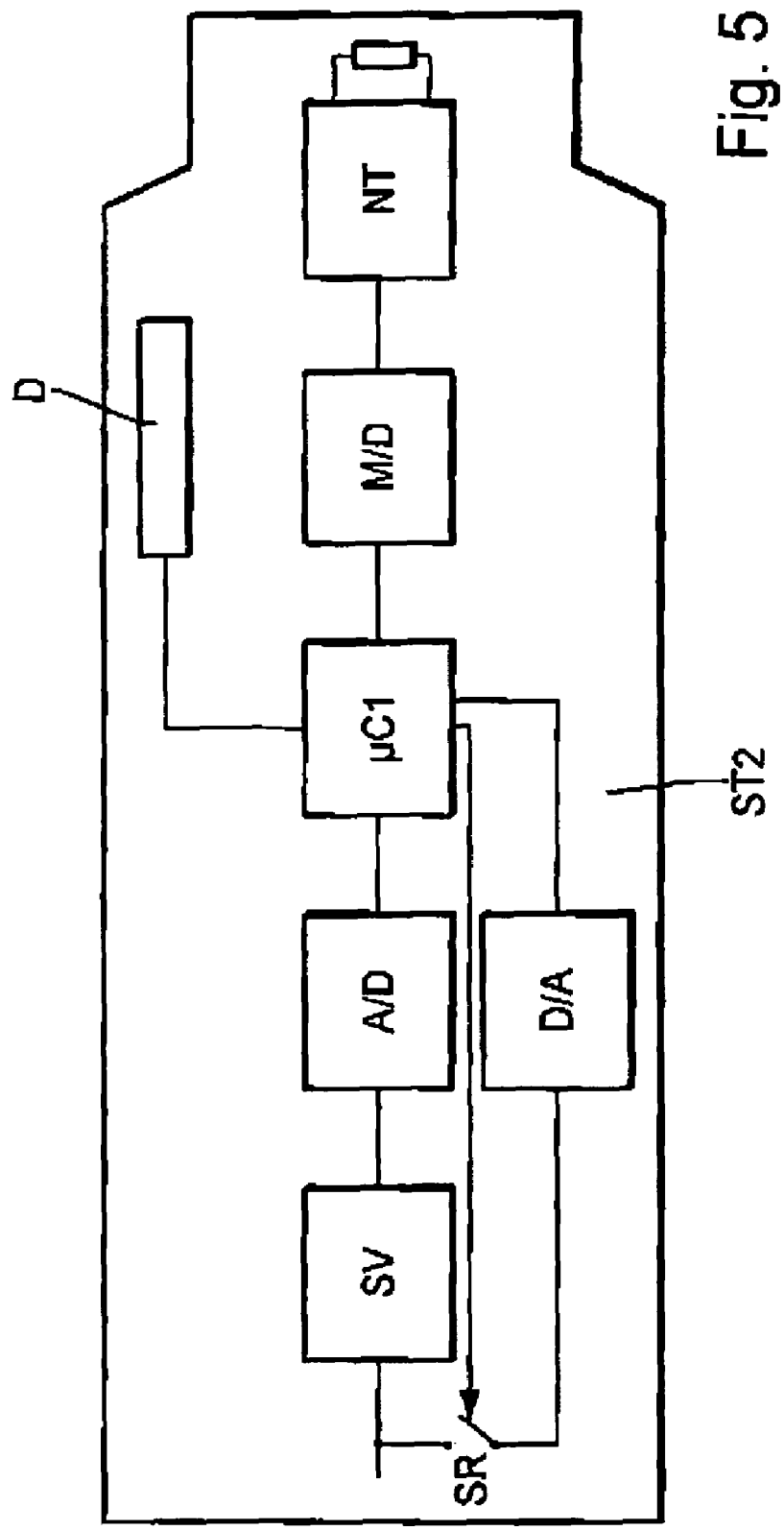
FIG. 5 pluggable module of the invention, for measured value simulation.

FIG. 5 schematically shows a pluggable module ST2, which serves for simulating a pH-value. Pluggable module ST2 is constructed similarly to sensor module SM. It has, however, no measured value pickup MA. In front of the analog signal processing unit SV is a switch SR, which is operated by the microcontroller μC1. Additionally, a digital-analog converter D/A is provided, which is likewise connected with the switch SR. With the help of the digital-analog converter D/A, a predetermined voltage can be produced, which simulates a measured voltage for the signal processing unit SV. The simulated measured value (pH-value) can be presented in the display D, which is likewise connected with the microcontroller μC1. Data transfer between pluggable module ST2 and e.g. a control room occurs via a sensor module head SMK. The two pluggable modules ST1, ST2 are embodied as key-ring pendants and can, therefore, be easily brought along, e.g. by service personnel.

The invention claimed is:

1. A pluggable module (STI) for a liquid-, or gas-, sensor, which sensor includes a sensor module (SM) and a sensor module head (SMK), which are pluggably connectable together and which enable, when plugged together, an exchange of data and energy via a galvanically decoupled, transfer zone, wherein:
   the pluggable module (ST1) is connectable with the sensor module (SM) and has a display unit, which serves for display of sensor data stored in the sensor module (SM), and
   the pluggable module (STI) and the sensor module (SM) enable, when plugged together, an exchange of data and energy via a galvanically decoupled transfer zone.

2. The pluggable module (STI) as claimed in claim 1, wherein:
   the pluggable module (STI) is embodied in the form of a key-ring pendant.

3. A pluggable module (STI) for a liquid-, or gas-, sensor, which sensor includes a sensor module (SM) and a sensor module head (SMK), which are pluggably connectable together and which enable, when plugged together, an exchange of data and energy via a galvanically decoupled, transfer zone, wherein:
   the pluggable module (ST1) is connectable with the sensor module (SM) and has a radio unit, which serves for transmission of sensor data stored in the sensor module (SM),
   the pluggable module (STI) and the sensor module (SM) enable, when plugged together, an exchange of data and energy via a galvanically decoupled transfer, and
   the pluggable module (STI) is embodied in the form of a key-ring pendant.

4. A pluggable module (STI) for a liquid-, or gas-, sensor, which sensor includes a sensor module (SM) and a sensor module head (SMK), which are pluggably connectable together and which enable, when plugged together, an exchange of data and energy via a galvanically decoupled, transfer zone, wherein:
   the pluggable module (ST1) is connectable with the sensor module (SM) and has a fieldbus interface (Profibus, Foundation Fieldbus, HART), which access to sensor data stored in the sensor module (SM) occurs,
   the pluggable module (STI) and the sensor module (SM) enable, when plugged together, an exchange of data and energy via a galvanically decoupled transfer zone, and
   the pluggable module (STI) is embodied in the form of a key-ring pendant.

5. A pluggable module (ST2) for a liquid-, or gas-, sensor, which sensor includes a sensor module (SM) and a sensor module head (SMK), which are pluggably connectable together and which enable, when plugged together, an exchange of data and energy via a galvanically decoupled transfer zone, wherein:
   the pluggable module (ST2) is connectable with the sensor module head (SMK) and has a simulation unit, which produces an analog signal value, which simulates a measured value and which is converted in a signal processing unit into a digital measured value, which is forwarded to the sensor module head (SMK), and
   the pluggable module (ST2) is embodied in the form of a key-ring pendant.

* * * * *

UNITED STATES PATENT AND TRADEMARK OFFICE
CERTIFICATE OF CORRECTION

PATENT NO. : 7,587,953 B2  Page 1 of 1
APPLICATION NO. : 10/572797
DATED : September 15, 2009
INVENTOR(S) : Detlev Wittmer It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 191 days.

Signed and Sealed this

Twenty-first Day of September, 2010

David J. Kappos
*Director of the United States Patent and Trademark Office*